United States Patent [19]

Tarcha et al.

[11] Patent Number: 5,266,498
[45] Date of Patent: Nov. 30, 1993

[54] LIGAND BINDING ASSAY FOR AN ANALYTE USING SURFACE-ENHANCED SCATTERING (SERS) SIGNAL

[75] Inventors: Peter J. Tarcha, Lake Villa; Thomas E. Rohr, Gurnee, both of Ill.; Therese Cotton, Ames, Iowa

[73] Assignee: Abbott Laboratories, Abbott Park, Ill.

[21] Appl. No.: 790,106

[22] Filed: Nov. 7, 1991

Related U.S. Application Data

[63] Continuation of Ser. No. 428,230, Oct. 27, 1989, abandoned.

[51] Int. Cl.$^5$ ............................................. G01N 33/553
[52] U.S. Cl. .................................... 436/525; 436/164; 436/173; 436/518; 436/801; 436/805
[58] Field of Search ............... 436/164, 173, 518, 525, 436/801, 805; 435/7.93, 7.94, 7.95

[56] References Cited

U.S. PATENT DOCUMENTS 4,781,458 11/1988 Angel et al.

FOREIGN PATENT DOCUMENTS 2156970 1/1984 United Kingdom.

OTHER PUBLICATIONS

Rohr et al. *Anal. Biochem.* 182: 388, 1989.
Kumar et al., *Biochem. J.* 175:727, 1978.
Curley et al. *Langmuir* 4:1021, 1988.
P. Gettings et al., "Variability of Nitro Group Protein Interaction in the 2, 4 Di Nitro Phenyl Binding Antibodies M-315 M-460 and X-25 Investigated by Resonance Raman Spectroscopy", Biochem Journal, 197, 119 (1981).
R. A. Copeland et al. "Surface-enhanced Raman Spectra Of An Active Flavo Enzyme: Glucoseoxidase and Riboflavin Binding Protein On Silver Particles—Potential Probe For Structure and Determination", Journal of American Chemical Society, 106, 3872 (1984).
N. S. Lee et al., "Surface-enhanced Raman Spectroscopy of the Catecholamine Neurotransmitters and Related Compounds", Anal. Chem., 60, 442, (1988).
E. Koglin et al., "Surface-Enhanced Raman Scattering of Biomolecules", Analytical Problems, Borgstedt, ed., (1986).
Product Specification, Effective Aug. 15, 1989, Corning 8612, "Polarcor Polarizing Filters".
F. Ni et al., "Surface-Enhanced Resonance Raman Study of Avidin-Dye Interactions: A Model for Chromophore-Containing Proteins", Journal of Raman Spectroscopy, 19, 429 (1988).
T. M. Cotton et al., "Surface-Enahnced Resonance Raman Scattering from Water-Soluble Porphyrins Adsorbed on a Silver Electrode", Journal of American Chemical Society, 104, 6528 (1982).
S. A. Soper et al., "Matrix-Isolated Surface-Enhanced Raman Spectroscopy (SERS): The Role of the Supporting Matrix", Applied Spectroscopy, 43, 1180, (1989).
E. W. Thomas et al., "Resonance Raman Spectroscopic Studies of 2-(4'-hydroxyphenylazo)-benzoic Acid and Some Substituted Analogs—II, Binding to Avidin and Bovine Serum Albumin", Spectrochimica Acta; 35A, 1251 (1979).

(List continued on next page.)

*Primary Examiner*—Esther L. Kepplinger
*Assistant Examiner*—Christopher L. Chin
*Attorney, Agent, or Firm*—Richard D. Schmidt

[57] ABSTRACT

An assay for an analyte in a test sample that uses a ligand binding reaction between the analyte and a specific binding member or a binding member pair that includes one binding member having a Raman active reporter. The analyte can be assayed by measurement of the Raman scattering signal of the Raman-active reporter. The Raman scattering signal can be either a noon-enhanced Raman scattering signal or a Raman scattering signal that is enhanced by a surface capable of enhancing that Raman scattering signal.

19 Claims, 7 Drawing Sheets

OTHER PUBLICATIONS

J. DeGroot, "Surface-Enhanced Resonance Raman Spectroscopy of Oxyhemoglobin Adsorbed onto Colloidal Silver", Journal of Physical Chemistry 91, 1693 (1987).

E. S. Brandt, "Analysis of Spectral Sensitizing Dyes in Photographic Films by Enhanced Raman Scattering Spectroscopy", Analytical Chemistry, 61, 391 (1989).

R. E. Holt, "Surface-Enhanced Resonance Raman and Electrochemical Investigation of Glucose Oxidase Catalysis at a Silver Electrode" Journal of Am. Chem. Soc., 111, 2815 (1989).

T. E. Rohr, "Application of Surface-Enhanced Raman Spectroscopy to Immunoassay" J. Cell Biology, 107(6) Part 3, 214A (Dec. 1988).

J. J. Laserna, "Studies of Sample Preparation for Surfaced-Enhanced Raman Spectrometry or Silver Hydrosois" Anal. Chim. Acta., 200, Issue 1, 469, (1987).

G. J. Thomas, Jr., "Elucidation of Protein and DNA Interactions in Viruses and Repressor/Operator Complexes using Laser Raman and Genetic Engineering Methods", In Laser Scattering Spectroscopy of Biological Objects; Proceedings of the International Conference Held in Prague (Jul. 6–10, 1986) Elsevier, New York, (1987).

Y. Ozaki, "Potential of Raman Spectroscopy in Medical Science" Laser Scattering Spectroscopy of Biological Objects: Proceedings of the International Conference, Held in Prague, (Jul. 6–10, 1987) Elsevier, New York, (1987).

P. B. Daniels, "Surface Plasmon Resonance Applied to Immunosensing", Sensors and Actuators, 15, 11 (1988).

LIGAND BINDING ASSAY FOR AN ANALYTE USING SURFACE-ENHANCED SCATTERING (SERS) SIGNAL

This application is a continuation of application Ser. No. 07/428,230, filed Oct. 27, 1989, now abandoned.

BACKGROUND OF THE INVENTION

A. Field of the Invention

This invention entails a novel method, apparatus, and materials for the measurement of binding between molecules which have mutual affinity. The affinity of binding displayed by certain molecules (referred to here as binding molecules) towards other specific molecules (referred to here as ligands) is used commonly as the basis of assays to measure the quantity of a particular binding molecule or ligand in a sample.

The two molecules involved in forming a binding molecule-ligand complex are also referred to as a specific binding pair. One member of a specific binding pair is referred to as a specific binding member. This invention includes methods for performing the assays using specific binding pairs of binding molecules and ligands, with Raman light scattering as the method of detecting binding. This invention also includes materials used in performing the assays and instrumentation used to perform the assays.

An assay is a test (1) to detect the presence of a substance in a sample, (2) to identify a substance in a sample, or (3) to measure the amount of a substance in a sample. In the terminology of this field, the substance that the assay is designed to detect (or identify or measure) is called an "analyte" (a glossary of some of the terms used herein is included as an appendix to this application).

Ligand binding assays are especially relevant to medical diagnostics. In modern medical practice, ligand binding assays are routinely run on patients' blood, urine, saliva, etc. in order to determine the presence or levels of antibodies, antigens, hormones, medications, poisons, toxins, illegal drugs, etc.

New, better, cheaper, and faster assays can advance the level of health care. Such assays can provide a physician with more and better information about a patient and do so consistent with reasonable cost. In addition, by making assays easier and cheaper, a higher level of health care can be extended to less developed parts of the world. Ligand binding assays are also being used to monitor groundwater contamination, toxins and pesticides in foods, industrial biological processes, and in many areas of biological research.

B. Present Ligand Binding Assays

For many assays it is required that minute quantities of a certain substance (the analyte) be detected and measured in the presence of much larger quantities of other substances. This is possible because the high affinity a binding molecule can have for a ligand can result in a high degree of specificity of binding for that particular ligand, irrespective of the presence of other substances. The most common ligand binding assays are immunoassays.

In an immunoassay, an antibody serves as a binding molecule which specifically binds an antigen, which serves as the ligand, thereby forming a specific binding pair. In order to measure the extent of the antibody/antigen binding, one member of the specific binding pair is tagged or labeled with a traceable substance. The unique properties of the traceable substance allow its presence, and hence the presence of the specific binding member to which it is attached, to be detected or measured. The labeled member of the specific binding pair is referred to as the indicator reagent.

In a direct immunoassay, the quantity of indicator reagent bound to the other member of the specific binding pair is measured. In an indirect immunoassay, the degree of inhibition of binding of the indicator reagent to the other member of the specific binding member by the analyte is measured.

The individual members of a specific binding pair do not have to be antigens or antibodies, however. Any two molecules having affinity for each other may comprise a specific binding pair and may form the basis of a ligand-binding assay. Other examples of such specific binding pairs are: lectins and the complex carbohydrates to which they bind, hormones and their receptors, any effector molecule and its receptor, binding molecules designed through molecular modeling and synthesized specifically to bind another molecule, and other molecules with mutual affinity such as avidin and biotin.

Two commonly-used immunoreaction techniques are radioimmunoassay (RIA) and enzyme immunoassay (EIA), both of which employ a labeled specific binding member as an indicator reagent. RIA uses a radioactive isotope as the traceable substance attached to a specific binding member. Because the radioactive isotope can be detected in very small amounts, it can be used to detect or quantitate small amounts of analyte. There are, however, a number of substantial drawbacks associated with RIA. These drawbacks include the special facilities and extreme caution that are required in handling radioactive materials, the high costs of such reagents and their unique disposal requirements.

EIA uses an enzyme as the label attached to a specific binding member. This enzyme-labeled specific binding member then serves as the indicator reagent, and enzymatic activity is used to detect its binding. While EIA does not have some of the same disadvantages as RIA, EIA techniques require the addition of substrate materials to elicit the detectable enzyme reaction. In addition, enzyme stability and rate of substrate turnover are temperature sensitive, the former decreasing and the latter increasing with temperature.

A drawback common to all of these assay configurations is the necessity of separating unbound labeled reagent from that bound to the analyte. This usually entails wash steps which are tedious when the assays are performed manually and require complicated robotics in automated formats.

Immunoassays may also be performed by automated instruments. Examples of such instruments are the TDx and IM$_x$ analyzers which are commercially available from Abbott Laboratories, Abbott Park, Ill. The TDx and Im$_x$ are used to measure analyte concentrations in biological fluids such as serum, plasma and whole blood.

Other types of assays use the so-called "dipstick" and "flowthrough" methods. With these methods, a test sample is applied to the "dipstick" or "flowthrough" device, and the presence of the analyte is indicated by a visually detectable signal generated by a color forming reaction. Flowthrough devices generally use a porous material with a reagent-containing matrix layered thereon or incorporated therein. Test sample is applied to the device and flows through the porous material. The analyte in the sample then reacts with the reagent(s) to produce a detectable signal on the porous material. Such devices have proven useful for the qualitative determination of the presence of analytes.

More recently, assay techniques using metallic sol particles have been developed. The specific binding member to be labeled is coated onto the metal sol particles by absorption and the metal sol particles become the label. Localization of these labeled binding members on a solid support via an immunoreaction can produce a signal that is visually detectable, as well as measurable by an instrument.

Fluorescent and visible dyes and spin labels have also been used as labels in ligand binding assays.

All of these binding molecule-ligand assays have inherent drawbacks. The use of Raman light scattering as a means of detecting or measuring the presence of a labeled specific binding member, avoids some of these drawbacks, as explained below.

C. Rayleigh Light Scattering

For many years, it has been known that when certain molecules are illuminated by a beam of light, for example ultraviolet, visible, or near infrared, a small fraction of the incident photons are retained momentarily by some of the molecules, causing a transition of the energy levels of some of those molecules to higher vibrational levels of the ground electronic state. These higher vibrational levels are called virtual states. Most of the time, these are elastic collisions, and the molecules return to their original vibrational level by releasing photons. Photons are emitted in all directions at the same wavelength as the incident beam (i.e., they are scattered). This is called Rayleigh scattering.

D. Raman Light Scattering

In 1928, C. V. Raman discovered that when certain molecules are illuminated, a small percentage of the molecules which have retained a photon do not return to their original vibrational level after remitting the retained photon, but drop to a different vibrational level of the ground electronic state. The radiation emitted from these molecules will therefore be at a different energy and hence a different wavelength. This is referred to as Raman scattering.

If the molecule drops to a higher vibrational level of the ground electronic state, the photon emitted is at a lower energy or longer wavelength than that retained. This is referred to as Stokes-shifted Raman scattering. If a molecule is already at a higher vibrational state before it retains a photon, it can impart this extra energy to the remitted photon thereby returning to the ground state. In this case, the radiation emitted is of higher energy (and shorter wavelength) and is called anti-Stokes-shifted Raman scattering. In any set of molecules under normal conditions, the number of molecules at ground state is always much greater than those at an excited state, so the odds of an incident photon hitting an excited molecule and being scattered with more energy than it carried upon collision is very small. Therefore, photon scattering at frequencies higher than that of the incident photons (anti-Stokes frequencies) is minor relative to that at frequencies lower than that of the incident photons (Stokes frequencies). Consequently, it is the Stokes frequencies that are usually analyzed.

The amount of energy lost to or gained from a molecule in this way is quantized, resulting in the scattered photons having discrete wavelength shifts. These wavelength shifts can be measured by a spectrometer. Raman scattering was considered to have the potential to be useful as an analytical tool to identify certain molecules, and as a means of studying molecular structure. However, other methods, such as infrared spectroscopy, proved to be more useful.

E. Resonance Raman Scattering

Interest in Raman spectroscopy was renewed with the advent of the laser as a light source. Its intense coherent light overcame some of the sensitivity drawbacks of Raman spectroscopy. Moreover, it was discovered that when the wavelength of the incident light is at or near the maximum absorption frequency of the molecule, and hence can cause electronic as well as vibrational transitions in the molecules, resonance Raman scattering is observed. Wit resonance Raman scattering, the re-emitted photons still show the differences in vibrational energy associated with Raman scattering. However, with resonance Raman scattering, the electronic vibrational absorption is approximately 1000 times more efficient. Even with the increased signal from resonance Raman scattering, its usefulness as an analytic tool was limited due to its still comparatively weak signal. The relatively recent discovery of the surface enhancement effect, however, has provided a means to further dramatically enhance Raman scattering intensity.

F. Surface Enhanced Raman Scattering

A significant increase in the intensity of Raman light scattering can be observed when molecules are brought into close proximity to (but not necessarily in contact with) certain metal surfaces. The metal surfaces need to be "roughened" or coated with minute metal particles. Metal colloids also show this signal enhancement effect. The increase in intensity can be on the order of several million-fold or more. In 1974, Dr. Richard P. Van Duyne was the first to recognize this effect as a unique phenomenon and coined the term "surface enhanced Raman scattering" (SERS).

The cause of the SERS effect is not completely understood; however, current thinking envisions at least two separate factors contributing to SERS. First, the metal surface contains minute irregularities. These irregularities can be thought of as spheres (in a colloid, they are spheroidal or nearly so). Those particles with diameters of approximately 1/10th the wavelength of the incident light are considered to contribute most to the effect. The incident photons induce a field across the particles which, being metal, have very mobile electrons.

In certain configurations of metal surfaces or particles, groups of surface electrons can be made to oscillate in a collective fashion in response to an applied oscillating electromagnetic field. Such a group of collectively oscillating electrons is called a "plasmon." The incident photons supply this oscillating electromagnetic field. The induction of an oscillating dipole moment in a molecule by incident light is the source of the Raman scattering. The effect of the resonant oscillation of the surface plasmons is to cause a large increase in the electromagnetic field strength in the vicinity of the metal surface. This results in an enhancement of the oscillating dipole induced in the scattering molecule and hence increases the intensity of the Raman scattered light. The effect is to increase the apparent intensity of the incident light in the vicinity of the particles.

A second factor considered to contribute to the SERS effect is molecular imaging. A molecule with a dipole moment, which is in close proximity to a metallic surface, will induce an image of itself on that surface of opposite polarity (i.e., a "shadow" dipole on the plasmon). The proximity of that image is thought to enhance the power of the molecules to scatter light. Put another way, this coupling of a molecule having an induced or distorted dipole moment, to the surface plasmons, greatly enhances the excitation probability. The result is a very large increase in the efficiency of Raman light scattered by the surface-absorbed molecules.

The SERS effect can be enhanced through combination with the resonance Raman effect. The surface-enhanced Raman scattering effect is even more intense if the frequency of the excitation light is in resonance with a major absorption band of the molecule being illuminated. The resultant Surface Enhanced Resonance Raman Scattering (SERRS) effect can result in an enhancement in the intensity of the Raman scattering signal of seven orders of magnitude or more.

G. Application of SERS to Immunoassays

The SERS effect has been used by physical and analytical chemists to follow chemical reactions on electrode surfaces in order to study molecular surface structure and dynamics. Recently, the technique has also been applied to biological molecules containing Raman-active prosthetic groups, such as hemes.

Up until now, there has been no application of the SERS effect to immunodiagnostics.

Utilization of this technology in immunodiagnostics offers several unique advantages. Because of the extraordinary dependence of the SERS signal upon close association with a suitable surface, only those reporter molecules which have become immobilized on the SERS-active surface will contribute a significant signal, while the signal contribution of those remaining in solution will be negligible. Molecules bound in different environments or different orientations can exhibit differences in their Raman scattering characteristics. As a result, it is potentially possible to differentiate among the Raman scattering spectra of free species in solution, bound species in solution, surface absorbed species and species attached to a surface via a specific ligand binding reaction.

In view of these unique characteristics Raman-based ligand binding assays can be designed which eliminate the need to remove excess unbound scattering molecules.

SUMMARY OF THE INVENTION

According to one feature of the present invention there is provided a method for assaying an analyte in a test sample by first combining the test sample with a specific binding pair having an affinity for the analyte being assayed and in which one specific binding pair member includes a Raman-active reporter. Then, the Raman spectra of the resultant is measured.

According to another feature of the present invention, there is provided a method for assaying an analyte in a test sample by combining the test sample with a specific binding pair having an affinity for the analyte being assayed and in which one specific binding pair member includes a Raman-active reporter and the other specific binding pair member is bound to a metallic surface. Then, the Raman spectra of the resultant is measured.

According to another feature of the present invention, there are provided surfaces, reporter labels, and excitation sources for use in a method for assaying an analyte in a test sample in which the test sample is first combined with a specific binding pair having an affinity for the analyte being assayed and in which one specific binding pair member includes a Raman-active reporter and the other specific binding pair member is bound to a metallic surface after which the Raman spectra of the resultant is measured.

According to yet another feature of the present invention, there is provided an analyzer for assaying an analyte in a test sample in which the test sample is combined with a specific binding pair having an affinity for the analyte being assayed and in which one specific binding pair member includes a Raman-active reporter and the other specific binding pair member is bound to a metallic surface after which the Raman spectra of the resultant is measured.

DETAILED DESCRIPTION OF THE PRESENTLY PREFERRED EMBODIMENTS

A. Alternative Preferred Embodiments

1. Surfaces

Figure 1:
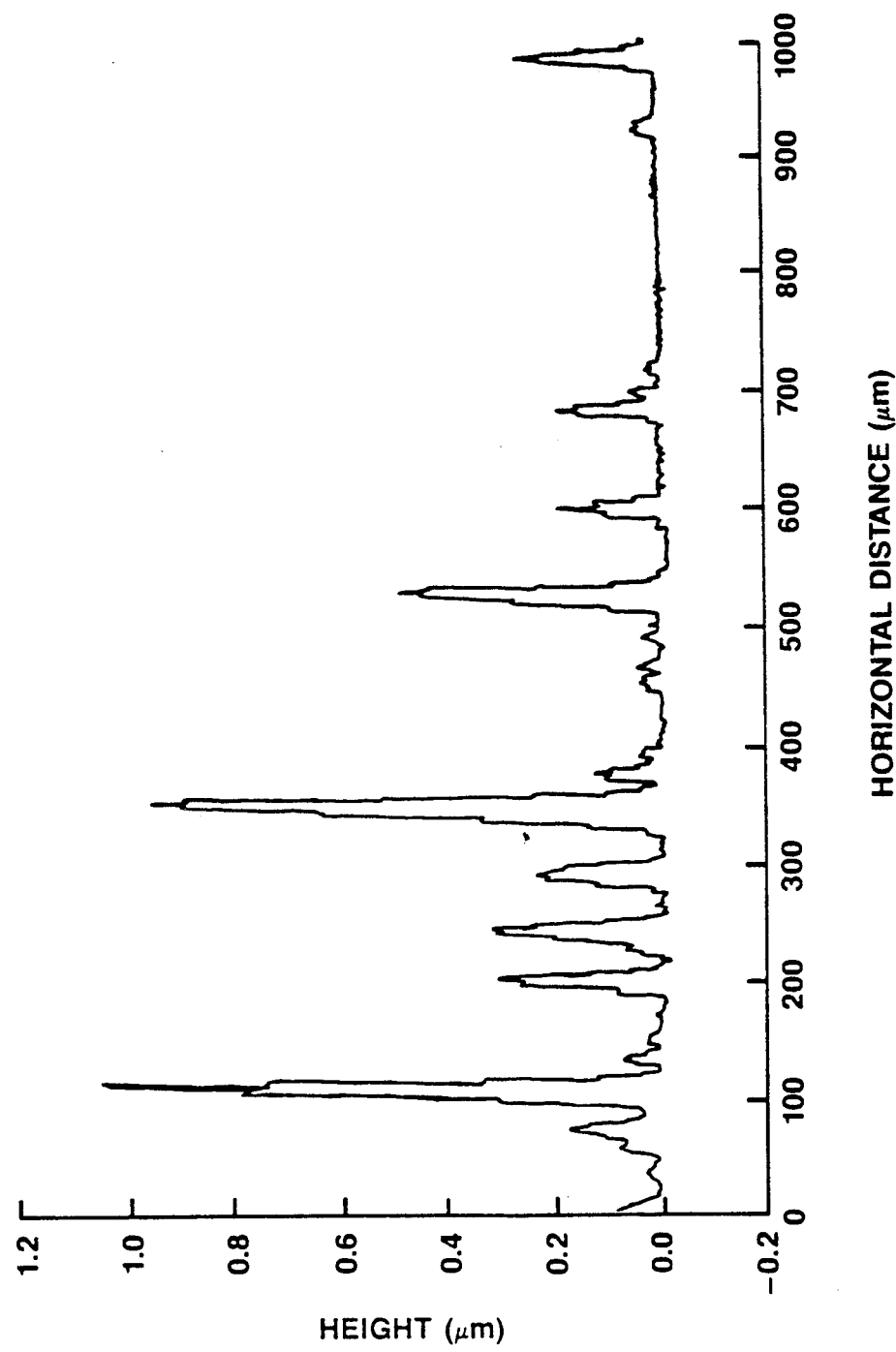
FIG. 1 is a profilometer tracing of an intact, chemically deposited silver film surface.

Many metallic materials and configurations may be used for the SERS active surface. These materials (for example, silver, gold, copper, platinum etc.) could take the form of flat surfaces (electrodes, strips, slides, etc.) or dispersed colloids, particles, droplets, i.e. mercury, or inert support structures of silica, plastic, glass, paper, or other materials which may be in the form of macroscopically flat or textured (ruled, etched, dimpled, or molded) pieces, slides, strips or spheroids, or fibers which are coated with the active material (e.g., silver, gold, etc.) such that they will support the surface enhancement of Raman scattering described above. The surface or layer giving the enhancement can also be coated with another material (silica, plastic, oxide, etc.) to which the specific binding member is attached.

The presence of photoexcitable surface plasmons is generally considered necessary for surface enhancement. In order for surface plasmons to surface so that plasmon emission can SERS effect, its surface plasmons must be localized so that their resident energy is not dispersed. This can be accomplished by preparing a roughened surface composed of small particles. In practice, the surface of a solid piece of metal can be electrochemically "roughened". As in the examples which follow silver particles can be precipitated from solution onto a support, or silver can be deposited on a support by evaporation or sputter coating. Silver coated replica gratings also give strong SERS enhancement as do silver coated surfaces which have been textured with bumps or posts, or coated with spheres, then coated with silver.

An attractive surface for SERRS based assays is metal colloid. A metal colloid combines a very strong SERS activity with the advantage of a liquid medium that can readily be handled. The combination of a SERS readout and a colloidal reagent would allow assays to be run in a manner similar to that used for present clinical chemistry analysis.

Another surface that may be used in the present invention is a glass, impregnated with metal particles. This surface may be a silver-impregnated glass, used as a substrate upon which an improved surface enhancement of Raman scattering can be achieved. Certain glasses are commercially available which have a percentage of particulate silver embedded into their formulations. One glass in particular has been developed by Corning Glassworks which may be particularly applicable to SERRS. This product, Corning No. 8612 Polarcor, has elongated crystalline silver embedded into its surface to a depth of approximately 35 micrometers. The crystals are oriented in such a fashion so as to capitalize on the plasmon or resonant absorption effects of the silver conduction band electrons. This distribution and orientation of the silver in this product is intended to behave as a polarizer. Light of random polarization whose waves are aligned parallel to the long axes of the particles will be absorbed by the particles. Light waves whose polar orientation is perpendicular to the long axes will be transmitted unattenuated. The former case is the same condition that must exist to produce the pronounced enhancement as seen with SERRS. The SERRS enhancement is considerably greater on a microscopically roughened surface than on a polished surface. This roughening provides for a certain percentage of the total surface area to have proper angular and distance components to absorb the correspondingly polarized component of the impinging light waves. The aforementioned filled glass product satisfies the required conditions without the need for secondary processes like roughening. Side reactions such as oxidation, sulfide formation and photodegradation, which are known to occur on conventional pure silver surfaces, such as electrodes, are also avoided. The product is produced with particle dimensions and spacial distributions to accommodate a relatively broad band of wavelengths. Several discrete band passes throughout the red and near infrared portion of the optical radiation spectrum are available.

A specific binding member coupled to a Raman active label and bound near the surface of this glass can potentially exhibit an even more pronounced SERRS effect than in conventionally used surfaces for the following reasons: (a) the spacings between the silver surface and the label are more uniform (since the particle orientation is far less random); (b) the orientation of the silver particles with respect to the polarization of the light waves can be made optimal by physically moving the glass and (c) the incident light and the Rayleigh scattered light should be almost totally absorbed into the filled glass, simplifying the removal of reflected or Rayleigh scattered light from the Raman signal.

2. Attachment of Specific Binding Members to SERS-Active Surfaces

A specific binding member can be attached to the SERS-active surface by direct absorption, absorption through a linker arm covalently attached to the specific binding member, or by the covalent attachment of the specific binding member to a coating on the SERS-active surface directly or through a linker arm or by intercalation of the distal portion of a linker arm into the enhancing surface.

3. Reporter Molecules or Labels

The SERS-active reporter groups or labels can be any one of a number of molecules with distinctive Raman scattering patterns. Unlike the enzymes used in enzyme immunoassays, these labels species can be stable, simple, inexpensive molecules which can be chemically modified as required.

The following attributes enhance the effectiveness of the label in this application:
(a) A strong absorption band in the vicinity of the laser excitation wavelength (extinction coefficient near 10 to the four power).

(b) A functional group which will enable it to be covalently bound to a specific binding member.
(c) Photostability.
(d) Sufficient surface and resonance enhancement to allow detection limits in the subnanogram range.
(e) Minimal interference in the binding interaction between the labeled and unlabeled specific binding members.
(f) Minimal exhibition of strong fluorescence emission at the excitation wave length used.
(g) A relatively simple scattering pattern with a few intense peaks.
(h) Labels with scattering patterns which do not interfere with each other so several indicator molecules may be analyzed simultaneously.

Potential candidates for this reporter can be 4-(4-Aminophenylazo)phenylarsonic acid monosodium salt, arsenazo I, basic fuchsin, Chicago sky blue, direct red 81, disperse orange 3, HABA (2-(4-hydroxyphenylazo)-benzoic acid, erythrosin B, trypan blue, ponceau S, ponceau SS, 1,5-difluoro-2,4-dinitrobenzene, and p-dimethylaminoazobenzene. The chosen labels may be covalently attached to the specific binding members of interest.

4 Excitation Sources

In the preferred embodiment, a laser serves as the excitation source. The laser may be of an inexpensive type such as a helium-neon or diode laser. An operating lifetime of such lasers may be in excess of 50,000 hours.

In one embodiment, a diode laser is used to excite at or at the near IR spectrum, minimizing fluorescence interference. The excitation sources used need not necessarily be monochromatic and they also need not necessarily have to be of high intensity. Lamps may also be used.

The SERS effect can be excited by direct illumination of the surface or by evanescent waves from a waveguide beneath the plasmon-active surface.

5. Conjugates

Several different conjugates could be prepared from specific binding members having different specificities, each type with a different Raman active label having a distinctive scattering pattern. Mixing these conjugates in an assay would allow the simultaneous analysis of several different analytes in the same sample.

6 Detection

Several methods are available for detecting Raman scattering. These generally can be used with different types of spectrometers. In SERS, the primary measurement is one of light scattering intensity at particular wavelengths. SERS requires measuring wavelength-shifted scattering intensity in the presence of an intense background from the excitation beam. The use of a Raman-active substance having a large Stokes shift simplifies this measurement.

Several concepts for further simplifying the readout instrument have been proposed. These include the use of wavelength selective mirrors or holographic optical elements for scattered light collection.

Neither the angle of the incident light beam to the surface nor the position of the detector is critical using SERS. With flat surfaces positioning the surface of the laser beam at 60 degrees to the normal is commonly done and detection at either 90 degrees or 180 degrees to the beam are standard. SERS excitation can be performed in the near infrared range which would suppress intrinsic sample fluorescence. It may also be possible to perform SERS-based ligand binding assays using evanescent waves produced by optical waveguides.

No signal development time is required as readout begins immediately upon illumination and data can be collected for as long as desired without decay of signal unless the excitation light is extremely intense and chemical changes occur. The signal cannot overdevelop as in systems dependent on optical absorbance. Unlike fluorescent readout systems, SERS reporter groups will not self-quench so the signal can be enhanced by increasing the number of Raman reporter groups on the probe molecule. Fluorescent molecules near the SERS-active surface will actually be surface-quenched.

7. Instrumentation

The present invention is adaptable for use as an automatic analyzer. Since the instrument would monitor discrete Stokes shifted spectral lines, the need for an elaborate monochromator system is not necessary. Recent advances in state-of-the-art optics technology, such as holographic optical elements, allow the design of a suitable spectrometer with cost and complexity below that of the laboratory grade device.

Optical readout energies as result of SERS are above that which require ultra-sensitive photon counting devices. In fact, some SERRS spectrometers now in use incorporate silicon photodiode detectors. The optical efficiency of a typical monochromator used in a laboratory grade spectrometer is less than 10%. The advances in optical materials and components mentioned above should make possible two to three-fold increases in optical efficiency for a simple spectrometer dedicated to only a few specific spectral lines. This also addresses one of the previously major concerns, blocking of the Rayleigh scattering line. With blocking capabilities of newer filters on the order of $10^{-9}$, substitution of filters for one or more stages of the typical monochrometer system should be possible with significant cost savings.

B. EXAMPLES

Example 1

Preparation of Silver Surfaces

Support surfaces—Supports for the silver films were either flat, frosted glass pieces cut from microscope slides or quartz pieces cut from 4 in.×4 in.×20 mil. quartz substrates (General Electric type 124).

Chemical deposition—Silver was deposited on support surfaces by chemical reduction of silver nitrate as previously described by Ni and Cotton. Anal. Chem., 58, 3159, 1986. Tollens reagent was used to deposit the silver. Tollen's reagent was prepared in a small beaker by adding about 10 drops of fresh 5% NaOH solution to 10 mL of 2-3% $AgNO_3$ solution, whereupon a dark-brown AgOH precipitate is formed. This step is followed by dropwise addition of concentrated $NH_4OH$, at which point the precipitate redissolves. The beaker containing the clear Tollen's reagent was then placed in an ice bath. The frosted slides, which had been cleaned with nitric acid and distilled water, were placed into a Teflon frame, which could accommodate up to 15 slides, and placed into the Tollen's reagent. Three milliliters of 10% D-glucose was added to the solution with careful swirling to ensure mixing. The beaker was then removed from the ice bath and the solution allowed to reach room temperature. The beaker was placed into a water bath (55° C.) for 1 min followed by sonification for 1 min (Branson Sonicator, Model B22-4, 125 W). Finally, the silver-coated slides were rinsed several times with distilled water and again sonicated in distilled water for 30 s. The slides were then stored in distilled water for several hours prior to exposure to the adsorbate solution. By use of this procedure, slides were found to be stable in distilled water for up to 1 week.

The surfaces were yellow by transmitted light and demonstrated a coarse, granular appearance by scanning electron microscopy. A profilometer probe traversing the surface revealed many prominences, some approaching $10^3$ nm in height (FIG. 1). A cross section of the silver layer generated by scratching the surface with a stylus revealed it to be composed of partially fused spheroids approximately 100 nm in diameter. The step produced by scratching the silver off the substrate was found to be approximately 130 nm thick by profilometry.

Sputter coating—Quartz pieces were coated with a 75Å layer of silver by sputter coating using a Perkin-Elmer Randex Model 2400-85A while being rotated at 2.25 rpm for 4.5 min at a distance of 6.75 cm from the silver target. A forward power of 200 W and an argon flow rate of 12.25 cc/min were used. The silver film was transparent, blue by transmitted light. Scanning electron microscopy at a 2500-fold enlargement showed a fine-grained featureless surface.

Silver electrodes—Silver electrodes were prepared as previously described by Ni and Cotton, J. Raman Spectroscopy, 19, 429, 1988. They were constructed by sealing a flattened silver wire into a glass tube with Torr Seal. The exposed surface was rectangular with dimensions of approximately $2 \times 10$ mm. The electrode was polished with a slurry of 0.3 $\mu$m alumina in water on a mechanical polishing wheel. It was then rinsed and sonicated in distilled water to remove any alumina which might have adhered to the surface. This step was followed by roughening the electrode by an oxidation-reduction cycle (ORC), consisting of a double potential step from an initial potential of $-550$ mV to $+500$ mV and back to $-550$ mV in 0.1 M $Na_2SO_4$ solution An Ag-AgCl electrode was used as the reference electrode and a Pt electrode as the auxiliary electrode. The total charge passed during the oxidation step was equivalent to 25 mC cm$^{-2}$.

Silver colloids—Silver colloids were prepared by a modification of the procedure of Lee and Meisel, J. Phys. Chem. 86, 3391, 1982. 90 mg of silver nitrate was dissolved in 500 ml of distilled water and brought to boiling. A 10 ml solution of 1% sodium citrate was added all at once and the solution was stirred for 45 minutes, during which the silver colloid formed. The colloid was cooled to room temperature and stored for use without further purification. Typical particle sizes resulting from such preparations ranged from 20 to 80 nm.

Example 2

Preparation of Dye-Antibody Conjugates

Antibody (2 mg) was dissolved in 2 ml of 1% NaHCO$_3$, pH 8.6, and a 20-$\mu$l aliquot of a solution of 1 mg/ml 4-dimethylaminoazobenzene-4'-isothiocyanate in dimethylformamide (DMF) added. The mixture was stirred overnight, then desalted on a Sephadex G-25 (coarse) column ($1 \times 30$ cm). The ultraviolet and visible spectrum of the conjugate was compared to that of DAB and antibody alone, to determine the degree of substitution. The erythrosin-antibody conjugate was prepared the same Way, except the concentration of the erythrosin-isothiocyanate in DMF was 2.5 mg/ml.

Example 3

Nitration of Bovine Serum Albumin

A solution of 2 ml of 2,4-dinitrofluorobenzene in 150 ml of ethanol was mixed with a solution of 200 mg of bovine serum albumin of 10 g $Na_2CO_3$ in 100 ml distilled water. The mixture was stirred for 24 h and centrifuged at 3000 g for 20 min to remove precipitated material and the supernate was dialyzed against 6 liters of phosphate-buffered saline (PBS) for 23 h, then against two changes of 2 liters of PBS for 6 h each, and finally against two changes of 2 liters of distilled water, 6 h each. Dialysis was carried out at room temperature with 0.02% sodium azide present in all solutions except the final 2 liters of water. The contents of the dialysis bag were then lyophilized to dryness, yielding 136 mg. A sample was compressed into a potassium bromide pellet and its infrared spectrum recorded on a Nicolet 60 SX FT infrared spectrometer. A strong vibrational band at 1340 cm$^{-1}$, not inherent to native BSA, indicated introduction of nitro groups (data not shown). The degree of substitution of the BSA was determined by comparing the degree to which BSA and the nitro-BSA conjugate could be derivatized with 2,4,6-trinitrobenzenesulfonic acid (TNBSA). After reaction with TNBSA, the average absorbance at 330 nm of a 1 mg/ml solution of native BSA increased from 0 to 1.5 as the result of the derivitization of free amino groups. The same concentration of the DNP-BSA conjugate had an initial absorbance at 330 nm of 1.2 (from the DNP groups) which did not increase after incubation with the TNBSA reagent. It can be concluded that essentially all the available amino groups in the DNP-BSA conjugate had been derivatized with DNP by the Sanger's reagent.

Example 4

Generation of SERS Spectra by DNP-BSA Conjugate Absorbed to Silver Films

Figure 2:
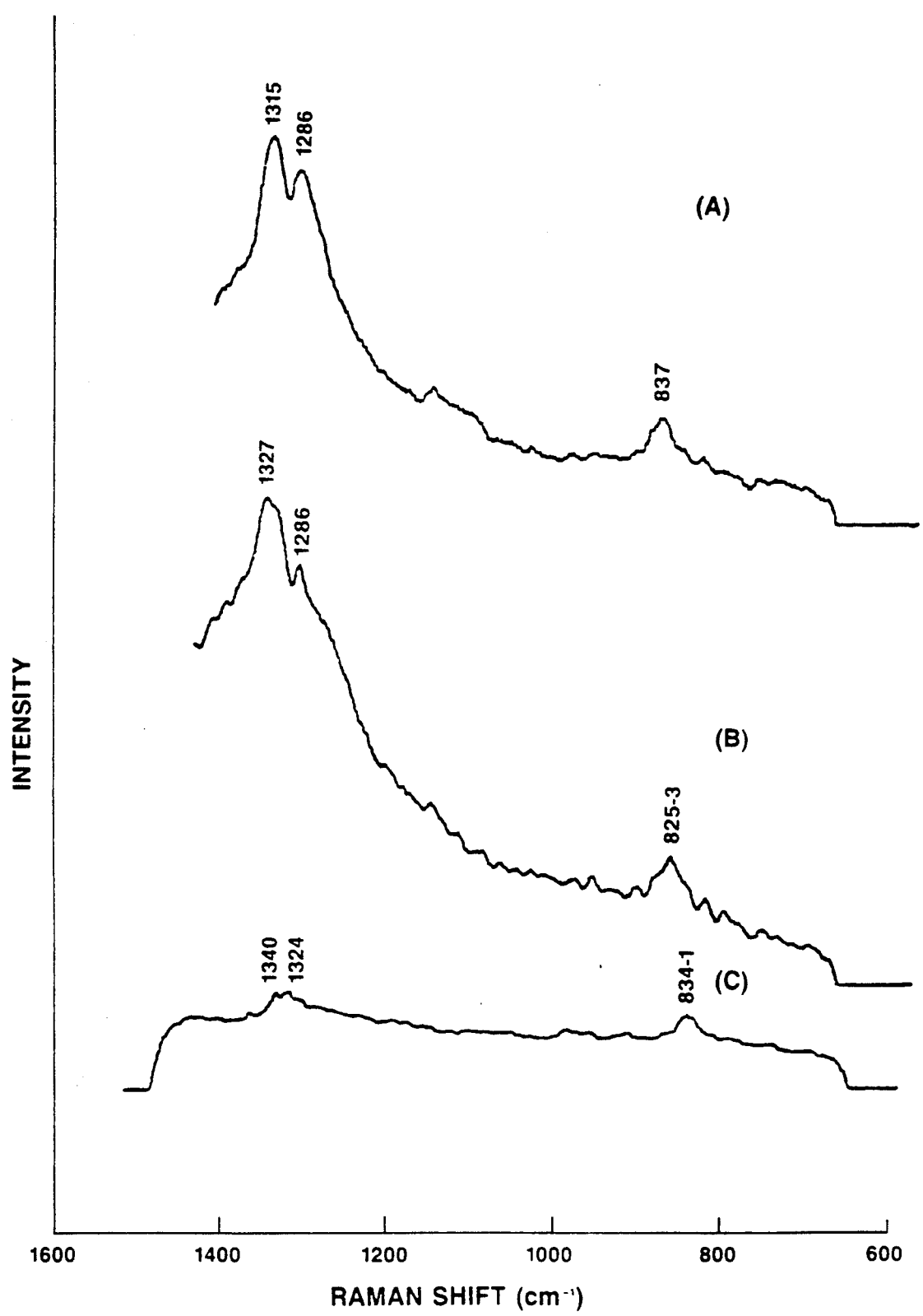
FIG. 2 is Raman spectra of (A) 2,4-dinitrobenzene solution, $10^{-3}$ M, in the presence of chemically deposited silver film, (B) 2,4-dinitrophenyl-BSA conjugate, $10^{-7}$ M with respect to DNP moieties, in the presence of a chemically deposited silver film, and (C) 2,4-dinitrobenzene, $10^{-3}$ M, in the absence of a silver film (ordinate expanded fourfold relative to A and B to enhance features). Spectra acquisition conditions: acquisition time, 19 s; power, 41 mW; excitation wavelength, 457.9 nm.

Freshly prepared silver-coated slides (chemically deposited) were incubated in buffer (pH 8.6) containing free DNB (FIG. 2A) or DNP-BSA conjugate (FIG. 2B), and SERS spectra obtained in both cases. Similar peak intensities were observed with free DNB at $10^{-3}$ M and DNP-BSA at $10^{-7}$ M with respect to DNP moieties ($2 \times 10^{-9}$ BSA), respectively. The four orders of magnitude difference in the specific intensity of surface-enhanced Raman light scatter observed between the free DNB and the DNP moieties of the DNP-BSA conjugate represents the greater ability of the latter to adsorb to the island film surface, thereby enabling its DNP moieties to display the SERS enhancement. A $10^{-3}$ M solution of DNB in the absence of an island film gave a very weak Raman spectrum (FIG. 2C).

Example 5

Use of a Raman-Active Dye to Demonstrate Surface-Enhanced Resonance Raman Spectroscopy An avidin molecule will also bind four molecules of the dye HABA, with an affinity constant of $K_a = 5.8 \times 10^6$ liter/mol at pH 7.0. Because this dye has a major spectral absorption at a wavelength which can be used to excite Raman light scattering (absorption maximum=495 nm when bound to avidin at pH 7) it is capable of SERRS.

Figure 3:
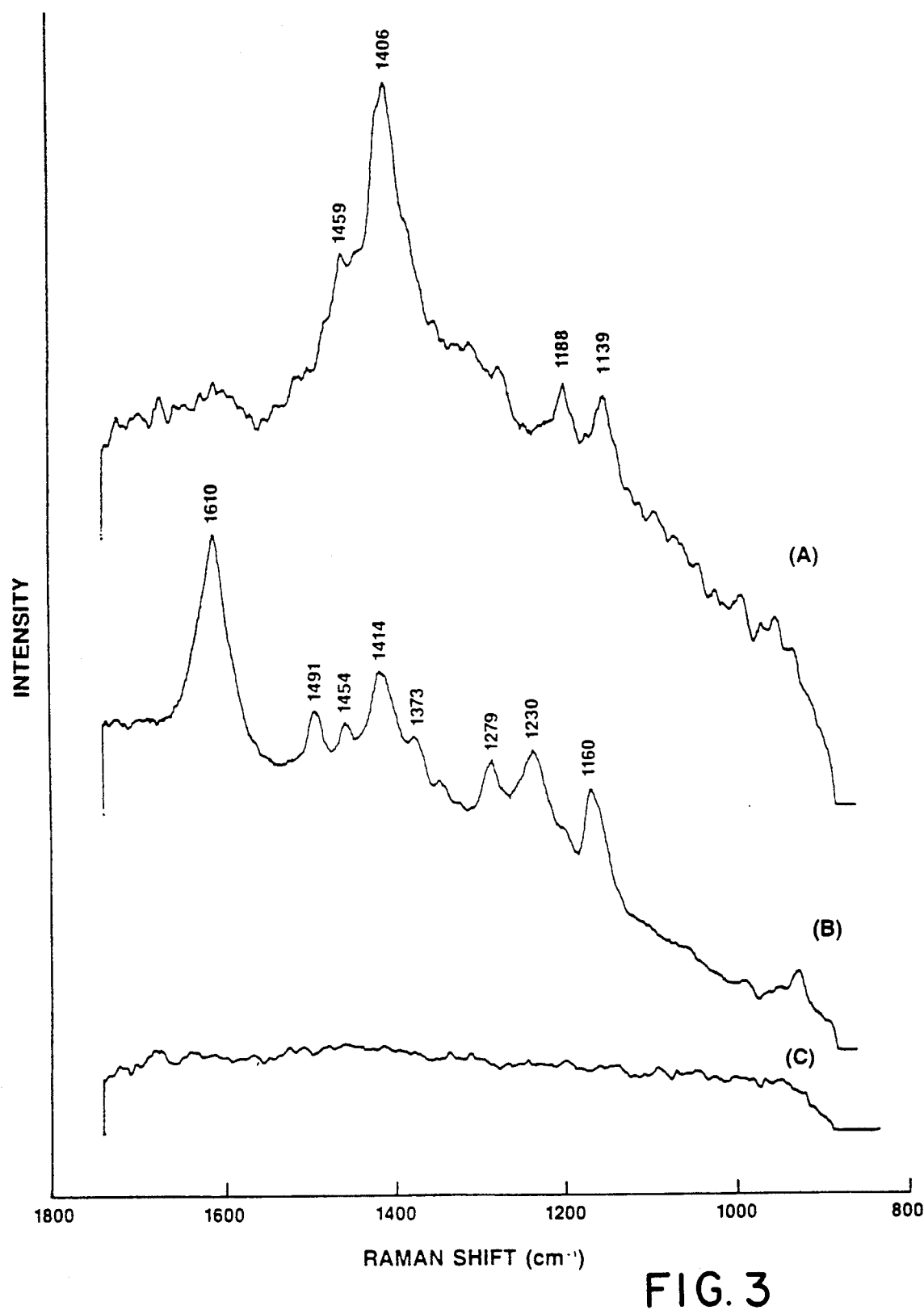
FIG. 3 is a SERRS spectrum obtained from a chemically deposited silver film incubated in (A) a 3 mM solution of HABA and (B) a $2.5 \times 10^{-5}$ M solution of avidin subsequently made 0.3 mM in HABA. No discernible spectrum was observed in this region from surface-absorbed avidin in the absence of HABA (C). Spectra acquisition conditions: acquisition time, 100 s; power, 50 MW; excitation wavelength, 457.9 nm.

Chemically deposited silver films, with and without prior coating with avidin, were incubated in a 3 mM solution of HABA. The films were then removed from the HABA solution and washed with PBS, and their Raman spectra taken. FIG. 3A is the spectrum obtained when HABA is adsorbed directly onto the surface of a silver film. A single major peak of light scattering intensity is observed at 1406 wavenumbers, with a shoulder at 1459 and minor peaks at 1188 and 1139 $cm^{-1}$. The spectrum shown in FIG. 3B was obtained when a silver film was first incubated for 20 min at room temperature in a $2.5 \times 10^{-5}$ M solution of avidin, then HABA added to a final concentration of approximately 0.3 mM, and incubation continued for an additional 20 min. Under these conditions, the major peak of Raman scattering intensity is observed at 1610 $cm^{-1}$, with several smaller peaks appearing between 1160 and 1491 $cm^{-1}$. The large peak at 1406 $cm^{-1}$, seen in the absence of avidin, is no longer observed. In the absence of HABA, an avidin-coated silver film gave no discernible spectrum in this region (FIG. 3C).

Example 6

Dye-Antibody Conjugates and Raman Readout in a Sandwich Immunoassay

Silver electrodes were incubated at 37° C. for 1 h in a 1 ml aliquots of a solution of 20 µg/ml anti-TSH antibody in 1% $NaHCO_3$, 8.6, and then overcoated for an additional hour in 1% BSA in PBS at 37° C. The films were then incubated for 1 h at 37° C. in the 0, 4, 10, 25 or 60 µIU/ml TSH antigen standards from the Abbott TSH EIA kit, Abbott No. 6207. After being washed three times with PBS, the films were transferred to test tubes containing 1 ml of the DAB-anti-TSH antibody conjugate at a concentration of 40 µg/ml, incubated for an additional hour at 37° C., washed again, and the SERRS spectra obtained.

Figure 4:
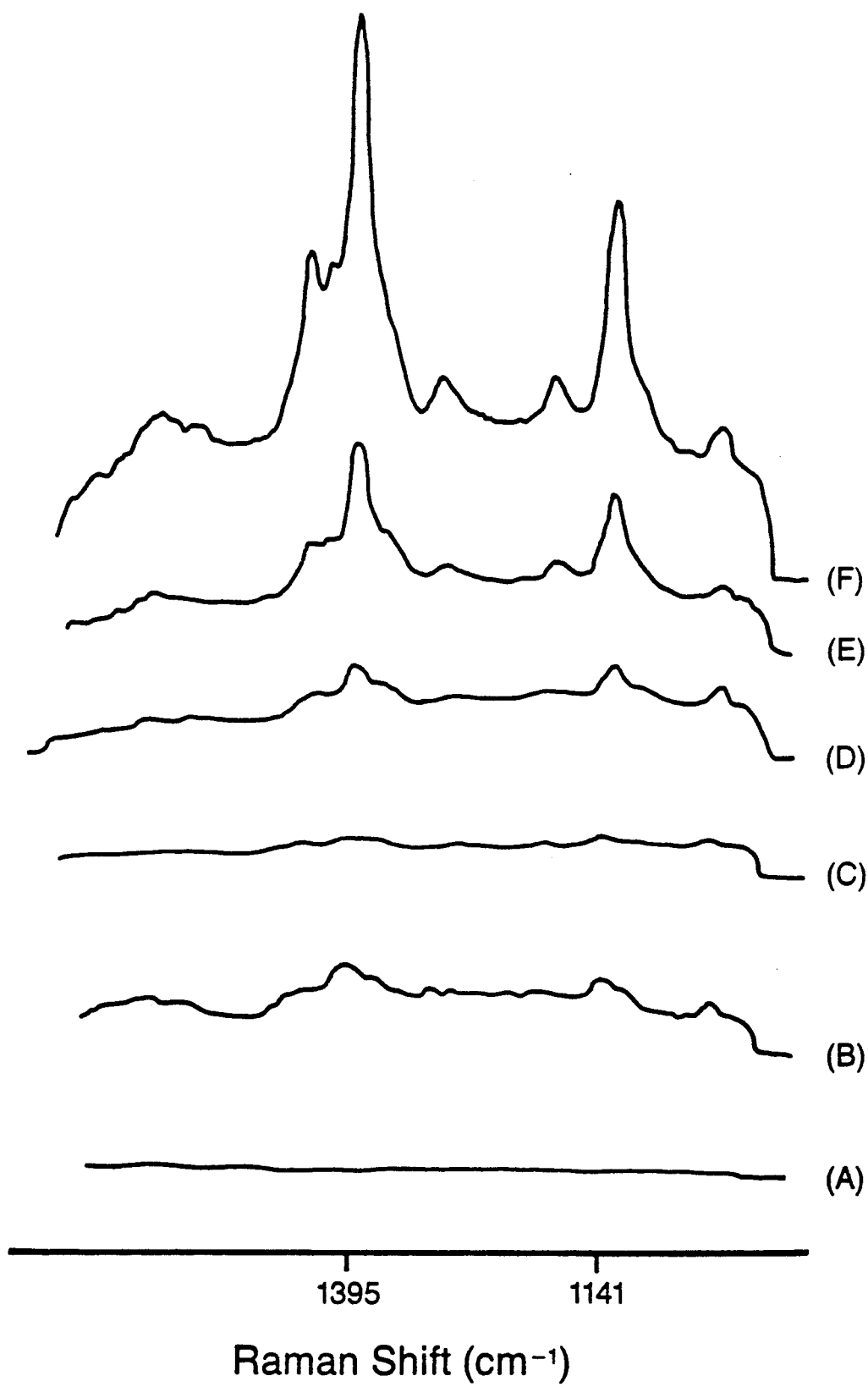
FIG. 4 is a combined plot of typical SERRS spectra obtained in a "sandwich" immunoassay for TSH antigen using a DAB-anti-TSH antibody conjugate. Silver electrodes coated with anti-TSH capture antibody were incubated with various concentrations of TSH antigen and then transferred to a 40 μg/ml solution of DAB-anti-TSH antibody conjugate. (A) SERRS spectrum of a 40 μg/ml solution of DAB-anti-TSH antibody conjugate in the absence of a silver surface. Plots (B), (C), (D), (E), and (F) show spectra obtained by incubating capture antibody-coated electrodes in solutions containing 0, 4, 10, 25 and 60 μIU of TSH antigen, respectively, followed by transfer to a 40 μg/ml solution of DAB-anti-TSH antibody conjugate.
Figure 5:
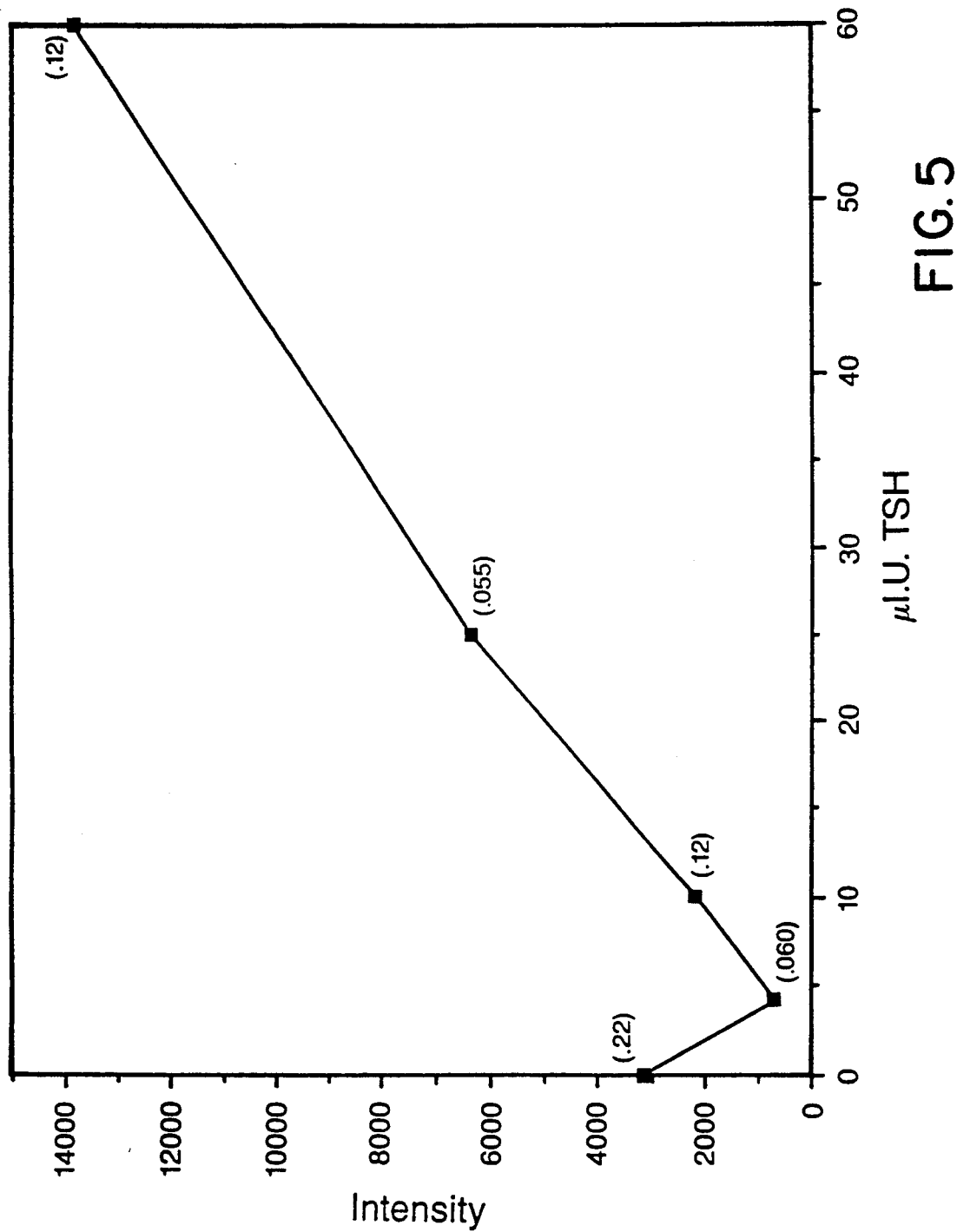
FIG. 5 is a plot of average SERRS intensity at 1141 $cm^{-1}$ as a function of TSH antigen concentration for known TSH standards. Values were obtained at five different places on the silver electrode and averaged. One electrode was used for each concentration of TSH antigen measured. Numbers in parentheses are the coefficients of variation (standard deviation/mean) for each concentration of analyte measured.
Figure 6:
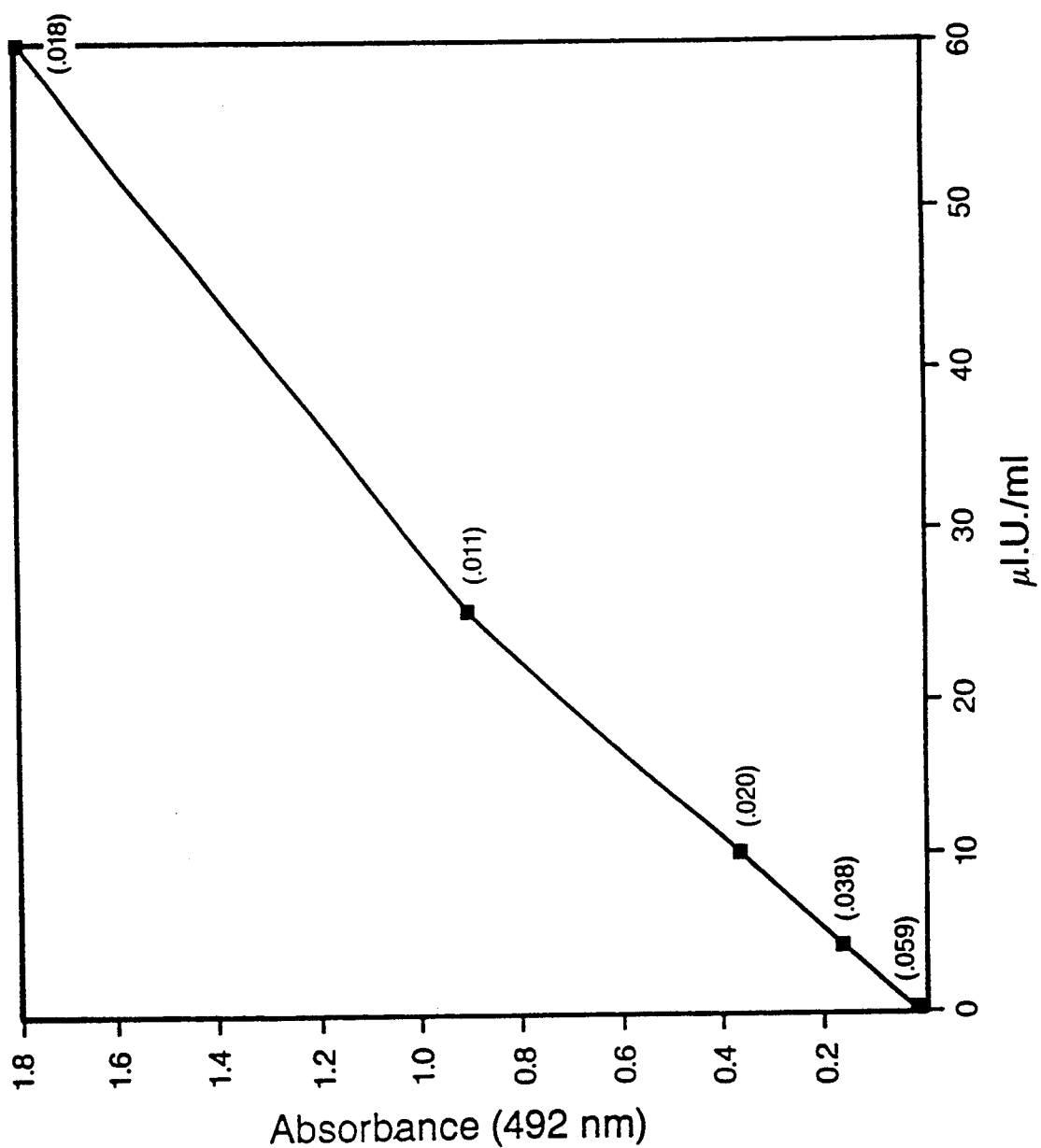
FIG. 6 is absorbance (492 nm) vs. TSH antigen concentration obtained using reagents from a commercial enzyme immunoassay kit (Abbott Labs No. 6207). Each data point represents the average of four determinations. The numbers in parentheses are the coefficients of variations (standard deviation/mean) for each concentration of TSH antigen measured.

SERRS spectra were obtained at five different places along each electrode and the results recorded. A combined plot of typical spectra obtained is shown in FIG. 4 for the five concentrations of TSH antigen studies. The averaged peak intensities at 1151 $cm^{-1}$ were used to generate a signal vs. concentration curve (FIG. 5). The same standards were also assayed using a modified commercial enzyme immunoassay (Abbott No. 6207, FIG. 6). Comparison of the two plots shows that the response obtained using the SERRS readout is similar to that given by the enzyme immunoassay, except for an anomalously high value for the zero antigen standard. This high zero reading was consistent upon reassay and must reflect a difference in composition between the zero standard and the other standards which does not effect results obtained by enzyme immunoassay.

Example 7

No Wash Immunoassay

A solution of 1% ascorbic acid was added to a silver sol (approximately 0.02% solids, 30 +/−5 nm particle diameter) to a final concentration of 1 mM. To individual 3.0 ml aliquots of sol were added 0.015 ml each of anti-human thyroid stimulating hormone antibody (1 mg/ml in phosphate buffered saline). The pH of the sol was then adjusted to 7.4 with phosphate buffer.

To one sample of antibody-coated sol was added 0.015 ml of 60 µl.U./ml human thyroid stimulating hormone (hTSH) standard. To the second sample was added 0.015 ml of 0 µl.U./ml hTSH standard. Both standards were contained in a pig serum matrix. 0.015 ml of p-dimethylaminoazobenezene-anti-TSH (DAB-ANTI-TSH) conjugate were added to each sample and incubated. After 20 minutes the surface-enhanced Raman spectra were recorded. The results showed approximately 2 times as intense a signal at a Raman shift of 1403 $cm^{-1}$, the strongest peak in the spectrum of the DAB dye, for the sample with the 60 µl.U./ml hTSH compared to the 0 µl.U./ml sample.

Example 8

Demonstration of SERS on Protein-Dye Conjugates using Near Infra-red Excitation

Figure 7:
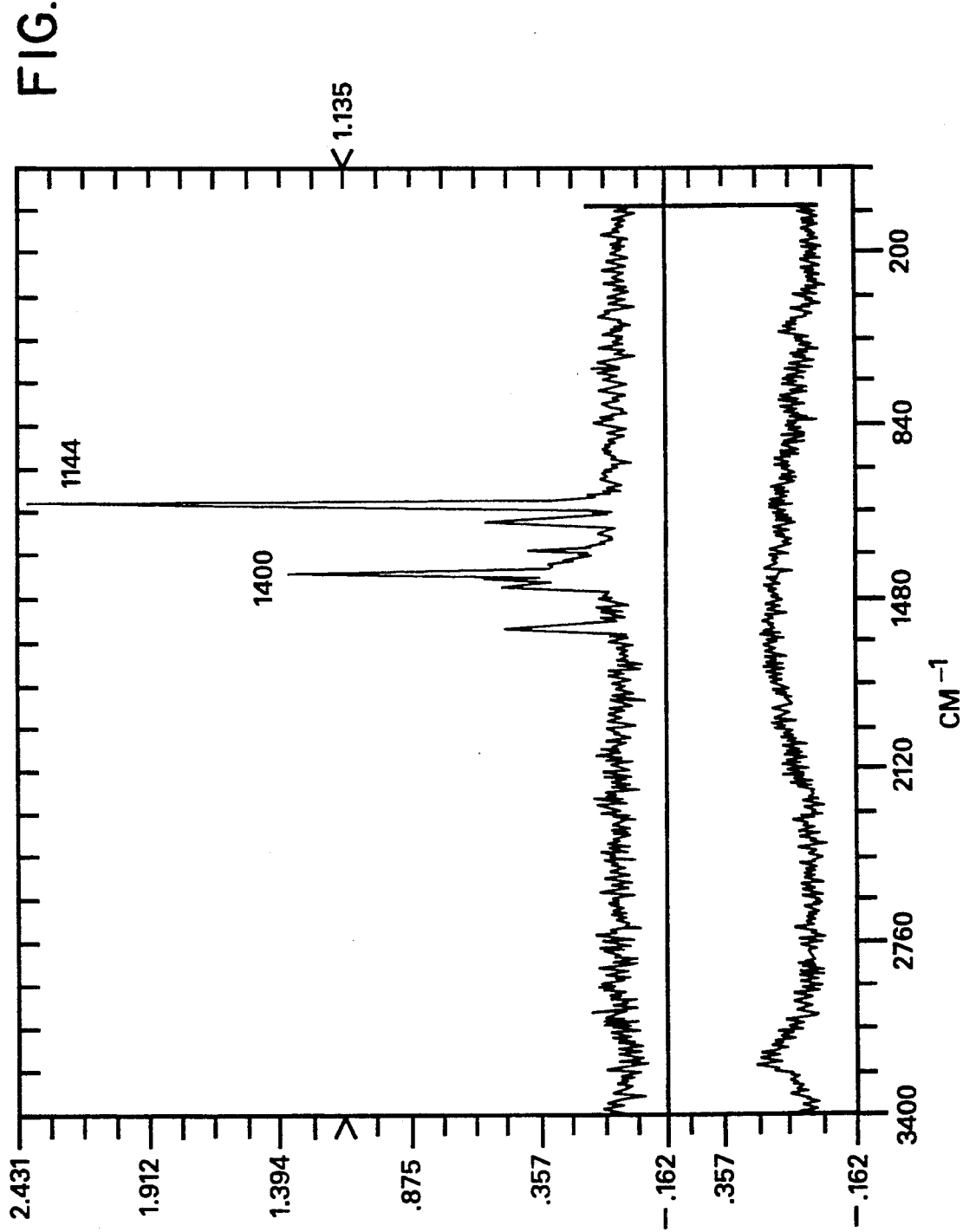
FIG. 7 is a SERS spectra using near IR excitation for A) spectrum of a blank silver film determined separately and added to solution state spectrum done in the absence of a silver surface, of the p-dimethylaminoazobenzene bovine serum albumin conjugate at 20 mg/ml, B) spectrum obtained by immersing the blank silver film in the aforementioned solution of the p-dimethylaminoazobenzene bovine serum albumin conjugate.

A chemically deposited silver film was emmersed in water in a cuvette and the SERS spectrum was recorded using a Bomem Raman spectrometer using excitation from a Nd:Yag laser at 1.06 nm. There was essentially no spectrum that was discernable from random noise. An aqueous solution of a p-dimethylaminoazobenzene-bovine serum albumin conjugate at 20 mg/ml was also scanned, but in the absence of any silver surface. Once again virtually no usable spectrum was distinguishable from the noise at the concentration used. This data was summed and plotted, and served as the blank for the experiment (FIG. 7A). The silver film used in the blank above was then added to the cuvette containing the dye-protein conjugate and the Raman spectrum taken. The data from the blank runs were subtracted giving the resultant SERS spectrum of the dye (FIG. 7B), which showed strong Raman scattering at Raman shifts of 1400 and 1412 $cm^{-1}$.

The foregoing description of the presently preferred embodiments of the present invention has been offered for purposes of illustration and description. It is not intended to limit the scope of the invention, which is defined by the appended claims and their equivalents. Various modifications and variations of the preferred embodiments are possible in light of the above teachings and will be apparent to persons skilled in the art. Such modifications and variations do not depart from the spirit or scope of the invention and it is therefore intended that the scope of the invention be defined by the appended claims, including all equivalents.

APPENDIX

"Analyte", as used herein, is the substance to be detected in the test sample using the present invention. The analyte can be any substance for which there exists a naturally occurring specific binding member (e.g., an antibody) or for which a specific binding member can be prepared, and the analyte can bind to one or more specific binding members in an assay. "Analyte" also includes any antigenic substances, haptens, antibodies, and combinations thereof. The analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

A "specific binding member", as used herein, is a member of a specific binding pair, i.e., two different molecules where one of the molecules through chemical or physical means specifically binds to the second molecule. In addition to antigen and antibody-specific binding pairs, other specific binding pairs include biotin and avidin, carbohydrates and lectins, complementary nucleotide sequences (including probe and captured nucleic acid sequences used in DNA hybridization assays to detect a target nucleic acid sequence), complementary peptide sequences, effector and receptor molecules, enzyme cofactors and enzymes, enzyme inhibitors and enzymes, and the like. Furthermore, specific binding pairs can include members that are analogs of the original specific binding member. For example a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Indicator reagent", as used herein comprises a detectable label directly or indirectly attached to a specific binding member.

"Capture reagent", as used herein, is a specific binding member, capable of binding the analyte or indicator reagent, which can be directly or indirectly attached to a substantially solid material. The solid phase capture reagent complex can be used to separate the bound and unbound components of the assay.

"Ancillary specific binding member", as used herein, is a specific binding member used in addition to the specific binding members of the capture reagent and the indicator reagent and becomes a part of the final binding complex. One or more ancillary specific binding members can be used in an assay. For example, an ancillary specific binding member can be used in an assay where the indicator reagent is capable of binding the ancillary specific binding member which in turn is capable of binding the analyte.

"Analyte-analog". Analyte-analog, as used herein, refers to a substance which cross reacts with an analyte specific binding member although it may do so to a greater or lesser extent than does the analyte itself. The analyte-analog can include a modified analyte as well as a fragmented or synthetic portion of the analyte molecule so long as the analyte analog has at least one epitopic side in common with the analyte of interest.

"SERS (Surface Enhanced Raman Scattering)". The increase in Raman scattering exhibited by certain molecules in proximity to certain metal surfaces . . . .

"Surface Enhanced Resonance Raman Scattering". SERRS results when the adsorbate at a SERRS active surface is in resonance with the laser excitation wavelength. The resultant enhancement is the product of the resonance and surface enhancement.

Abbreviations

HABA. 2-[4-hydroxyphenylazo]benzoic acid.
DAB. p-dimethylaminoazobenzene.
IgG. Immunoglobulin G.
HTSH. Human thyroid stimulating hormone.
PBS. Phosphate buffered saline.
BSA. Bovine Serum Albumin.
TNBSA. 2,4,6 trinitrobenzene sulfonic acid.
DAB-ITC. 4-dimethylaminoazobenzene-4'-isothiocyanate.
DMF. Dimethyl formamide.
I.U. International units.

We claim:

1. A method for determining the presence or amount of an analyte in a test sample, comprising:

(a) contacting said test sample with an indicator reagent and a capture reagent to form a test mixture; said indicator reagent comprising a Raman active label directly or indirectly attached to a specific binding member wherein said Raman active label comprises at least one Raman active molecule providing a detectable or measurable Raman scattering signal when illuminated by a radiation capable of inducing a Raman scattering, wherein said specific binding member of said indicator reagent is specific for a substance selected from the group consisting of the analyte, the capture reagent and an ancillary specific binding member which specifically binds to said analyte directly or indirectly through one or more additional ancillary specific binding members; said capture reagent comprising a specific binding member directly or indirectly bound or attached to a surface capable of causing surface-enhanced Raman scattering (SERS), wherein said specific binding member of said capture reagent is specific for a substance selected from the group consisting of the analyte and the indicator reagent;

(b) allowing said indicator reagent and said capture reagent to bind to their respective specific binding pair members in said test mixture;

(c) inducing a Raman scattering signal by illuminating said surface with a radiation;

(d) measuring the intensity of said SERS signal resulting from said illumination of said surface; and (e) determining thereby the presence or amount of analyte in said test sample.

2. The method according to claim 1, wherein said SERS surface is in the form of a textured silver surface.

3. The method according to claim 1, wherein the SERS surface is in the form of a colloid.

4. The method of claim 1 wherein said indicator reagent binds to said analyte and said SERS signal correlates to the presence or quantity of said analyte bound to said capture reagent.

5. The method of claim 1 further comprising the step of separating the unbound indicator reagent from the bound indicator reagent prior to said measuring step.

6. The method of claim 5 wherein the bound and the unbound indicator reagent is separated by physical means.

7. The method of claim 6 wherein said physical means comprises a wash step.

8. The method of claim 5 wherein the quantity or presence of bound or unbound indicator reagent is determined by measurement of a SERS signal.

9. The method according to claim 1, wherein the test sample is a biological fluid.

10. A method for performing a ligand-binding assay for determining the presence or amount of an analyte in a test sample, comprising:

(a) contacting said test sample with an indicator reagent and a capture reagent to form a test mixture; said indicator reagent comprising a Raman active label directly or indirectly attached to a specific binding member wherein said Raman active label comprises at least one Raman active molecule providing a detectable or measurable Raman scattering signal when illuminated by a radiation capable of inducing a Raman scattering; wherein said specific binding member of said indicator reagent is specific for a substance selected from the group consisting of the analyte, the capture reagent, and an ancillary binding member which specifically binds to said analyte directly or indirectly through one or more additional ancillary specific binding members; said capture reagent comprising a specific binding member directly or indirectly bound or attached to a surface capable of causing a surface-enhanced Raman scattering (SERS) wherein said specific binding member of said capture reagent is specific for a substance selected from the group consisting of the analyte and the indicator reagent;

(b) allowing said indicator reagent and said capture reagent to bind to their respective specific binding pair members in said test mixture;

(c) illuminating said surface with a radiation so as to induce a SERS signal;

(d) measuring the intensity of Raman shift of said SERS signal resulting from the illumination of said surface; and (e) determining thereby the presence or amount of analyte in said test sample.

11. The method according to claim 10, wherein said SERS surface allows the differentiation of a bound Raman active label and a free unbound Raman active label during said measuring part of said method.

12. The method according to claim 10 wherein said SERS surface will support localized photoexcitable surface plasmons.

13. The method according to claim 10, wherein said SERS surface is in the form of a colloid.

14. The method according to claim 10, wherein said SERS surface is in the form of a textured silver surface.

15. The method according to claim 10, wherein the test sample is a biological fluid.

16. The method of claim 10, wherein said SERS signal or Raman shift correlates to the presence or quantity of said analyte bound to said capture regent.

17. The method of claim 10 further comprising the step of separating the unbound indicator reagent from the bound indicator reagent prior to said measuring step.

18. The method of claim 17 wherein the bound and the unbound indicator reagent is separated by physical means.

19. The method of claim 18, wherein said physical means comprises a wash step.

* * * * *